(12) United States Patent
Tsai

(10) Patent No.: US 9,259,558 B2
(45) Date of Patent: Feb. 16, 2016

(54) ASPIRATED WOUND DRESSING

(75) Inventor: Mingliang Lawrence Tsai, Las Vegas, NV (US)

(73) Assignee: CONVATEC TECHNOLOGIES, INC., Las Vegas, NV (US)

(*) Notice: Subject to any disclaimer, the term of this patent is extended or adjusted under 35 U.S.C. 154(b) by 880 days.

(21) Appl. No.: 13/144,617

(22) PCT Filed: Jan. 12, 2010

(86) PCT No.: PCT/US2010/020694
§ 371 (c)(1),
(2), (4) Date: Jul. 14, 2011

(87) PCT Pub. No.: WO2010/083135
PCT Pub. Date: Jul. 22, 2010

(65) Prior Publication Data
US 2011/0276016 A1 Nov. 10, 2011

(51) Int. Cl.
*A61M 1/00* (2006.01)
*A61M 27/00* (2006.01)

(52) U.S. Cl.
CPC ............ *A61M 27/00* (2013.01); *A61M 1/0031* (2013.01); *A61M 1/0088* (2013.01); *A61M 1/0092* (2014.02); *A61M 2205/3317* (2013.01); *A61M 2205/3344* (2013.01); *A61M 2205/3375* (2013.01)

(58) Field of Classification Search
USPC ................. 604/289, 290, 304, 305, 313, 319; 602/41, 56, 58
See application file for complete search history.

(56) References Cited

U.S. PATENT DOCUMENTS

| | | |
|---|---|---|
| 3,948,098 A | 4/1976 | Richardson et al. |
| 3,960,007 A | 6/1976 | Swensen |
| 4,354,180 A | 10/1982 | Harding |
| 4,747,166 A | 5/1988 | Kuntz |
| 4,969,880 A | 11/1990 | Zamierowski |
| 5,056,510 A | 10/1991 | Gilman |
| 5,576,619 A | 11/1996 | Buser et al. |
| 5,678,564 A | 10/1997 | Lawrence et al. |
| 5,954,705 A * | 9/1999 | Sawaki et al. .......... 604/385.101 |
| 2003/0212357 A1 | 11/2003 | Pace |
| 2004/0160328 A1 | 8/2004 | Becknell |
| 2005/0004534 A1 | 1/2005 | Lockwood et al. |
| 2006/0015081 A1 | 1/2006 | Suzuki et al. |
| 2006/0100594 A1 | 5/2006 | Adams et al. |
| 2008/0181969 A1* | 7/2008 | Blanton et al. ................ 424/618 |
| 2009/0216204 A1* | 8/2009 | Bhavaraju et al. ............ 604/290 |
| 2009/0312728 A1* | 12/2009 | Randolph et al. ............. 604/319 |
| 2010/0174250 A1* | 7/2010 | Hu et al. ........................ 604/319 |

FOREIGN PATENT DOCUMENTS

WO     WO9607380     3/1996

* cited by examiner

*Primary Examiner* — Melanie Hand
(74) *Attorney, Agent, or Firm* — Lorelei P. Westin, Esq.

(57) ABSTRACT

A wound dressing for an aspirated wound dressing system, with a wound interface region for contacting or facing a wound site; an aspiration port for receiving suction for aspiration of wound exudate; a liquid permeable pressure barrier disposed between the wound interface region and the aspiration port for substantially preventing application of negative pressure from the aspiration port to the wound interface region; at least one atmospheric vent for equalizing with atmosphere the pressure at the wound interface region; and a liquid sensor for sensing liquid within the wound dressing for controlling application of suction by the aspiration unit.

6 Claims, 4 Drawing Sheets

ASPIRATED WOUND DRESSING

CROSS-REFERENCE

This application is a U.S. National Stage of PCT/US2010/020694, filed Jan. 12, 2010; which claims the benefit of U.S. Ser. No. 61/144,885, filed Jan. 15, 2009; each of which is incorporated herein by reference in their entirety.

FIELD OF THE INVENTION

The present invention relates to the field of wound dressings that use aspiration to remove wound exudate.

BACKGROUND TO THE INVENTION

Wound exudate can be described as the liquid produced from chronic wounds, fistula, or acute wounds once haemostasis has been achieved. For centuries, the production of exudate was regarded as inevitable with certain types of wound, and inconsequential with respect to wound healing.

More recently, considerable attention has been given to the development of wound dressings that prevent the accumulation of large volumes of fluid within a wound, and also prevent the fluid from spreading over the surrounding healthy tissue. This is because excessive wound exudate can cause maceration of the peri-wound skin, which in turn can lead to infection. One technique known in the art is the application of suction through the wound dressing, to create and maintain negative pressure at the wound site. Negative pressure means pressure below surrounding atmospheric pressure. Such a technique is referred to in the art as Topical Negative Pressure (TNP). This is believed by some researchers to aid drainage of wound exudate away from the wound bed, reduce infection rates, and increase localized blood flow.

Maintaining negative pressure at the wound site may create some practical problems:

(i) The negative pressure may be able to draw tissue growth into the pores of a foam piece inside the wound dressing. This can result in discomfort to the patient during use of the device, especially when the dressing is removed or replaced. Removal or replacement of the dressing may also cause damage to that newly grown tissue.

(ii) The wound is vulnerable to drying out of wound exudate. This condition may be undesirable because exudate is believed to contain a complex mixture of bioactive molecules that have both positive and negative effects. While removal of excess exudate is desirable, removal of all exudate may hinder rather than aid wound healing. Proper use of the wound dressing may depend to a large extent on the expertise of medical staff in assessing the rate of production of wound exudate at the wound site, and adjusting the negative pressure accordingly. If frequent removal of the dressing is required to assess the state of the wound, this merely exacerbates discomfort caused by drawback (i) above.

Some of the potential drawbacks may be partly mitigated by the use of hydro-fiber as described in U.S. Patent Publication No. 2006/0100594.

The present invention has been devised bearing potential issues in mind.

SUMMARY OF THE INVENTION

Broadly speaking, one aspect of the invention is to apply suction for removing wound exudate, in a manner that avoids creation of substantial negative pressure at the wound site.

Such a technique permits effective removal of exudate, without the potential drawbacks of topical negative pressure. In particular, issues of tissue growth into the wound dressing itself, and associated patient discomfort, can be avoided.

In one form, the wound dressing comprises a liquid permeable pressure barrier between a point at which suction is applied, and the region interfacing a wound site. The barrier may, for example, comprise foam. The suction creates a pressure differential across the barrier and/or a local pressure gradient within the pressure barrier, thereby allowing efficient removal of liquid exudate that is in contact with or absorbed within the pressure barrier, without subjecting the wound site to substantial negative pressure.

Additionally or alternatively, the wound dressing comprises one or more vent passages for equalizing and/or stabilizing an interior space and/or wound interface region of the wound dressing at surrounding atmospheric pressure. The vent passages may, for example, comprise pores, capillaries, or porous material in an air-venting portion of the wound dressing, such as an air-venting backing or cover.

Another independent aspect of the invention is the use of porous material for an air-venting portion of an aspirated wound dressing. The porous material is permeable to air, but substantially impermeable to water vapor and liquid. This contrasts with the techniques of the prior art in which either (i) a cover layer of a dressing is made of semi-permeable material allowing moisture-vapor transpiration through the material, or (ii) the cover layer is generally impermeable for both gas and liquid. The term "semi-permeable" (as used for example in U.S. Pat. No. 4,969,880) means that a material is moisture-vapor permeable, but impermeable to liquids. The previous purpose of a moisture-vapor permeable membrane was to allow exudate moisture to evaporate through the membrane, as a way of promoting healing by preventing maceration of both normal skin and the wound.

In contrast, the present aspect of the invention may provide significant and surprising advantages not contemplated by the prior art. It enables air to enter the wound dressing, in order to equalize or stabilize the pressure with respect to external atmospheric pressure, which is significant as explained above for avoiding exposing the wound to substantial negative pressure. At the same time, outside sources of moisture and moisture vapor are prevented from ingress into the dressing, thereby reducing risk of contamination and infection. All removal of moisture occurs via the aspiration system, and there is no ingress of external moisture or moisture vapor, thereby making moisture level in the dressing easier to manage in a controllable, predictable way.

This aspect of the invention has an additional synergy when a liquid sensor is used for sensing liquid within the wound dressing. The idea of air-permeable material that obstructs passage therethrough of moisture vapor and liquid, in combination with a liquid sensor for controlling aspiration responsive to detection of liquid by the sensor, represents a fundamentally new approach for moisture and exudate management, while permitting entry of air into the dressing to equalize or stabilize the interior pressure with respect to external atmospheric pressure, and can avoid the negative effects of TNP.

In one form, a material is considered to be air-permeable, and substantially impermeable to moisture-vapor and liquid, when the moisture vapor transmission rate is no more than 1 gm/min at 10 mbar and when the air transmission rate in cc/min is at least 10 times greater than the moisture vapor transmission rate (MVTR in gm/min), more preferably at least 20 times greater, more preferably at least 50 times greater, more preferably at least 100 times greater. Preferably, the moisture vapor transmission rate is no more than 0.5 gm/min at 10 mbar. More preferably, the moisture vapor transmission rate is no more than 0.1 gm/min at 10 mbar. More preferably, the moisture vapor transmission rate is no more than 0.01 gm/min at 10 mbar.

An embodiment of a wound dressing for an aspirated wound dressing system, according to the present invention includes:
- a wound interface region for contacting or facing a wound site;
- an aspiration port for receiving suction for aspiration of wound exudate;
- a liquid permeable pressure barrier disposed between the wound interface region and the aspiration port for substantially preventing application of negative pressure from the aspiration port to the wound interface region;
- at least one atmospheric vent or porous material for equalizing with atmosphere the pressure at the wound interface region; and
- a liquid sensor for sensing liquid within the wound dressing, for controlling application of negative pressure by an aspiration unit.

These and other aspects of the invention are defined in the claims. While certain features and ideas are defined above and in the claims, protection may be claimed for any novel feature or idea disclosed herein and/or in the drawings whether or not emphasis has been placed thereon.

DETAILED DESCRIPTION OF PREFERRED EMBODIMENTS

Figure 1:
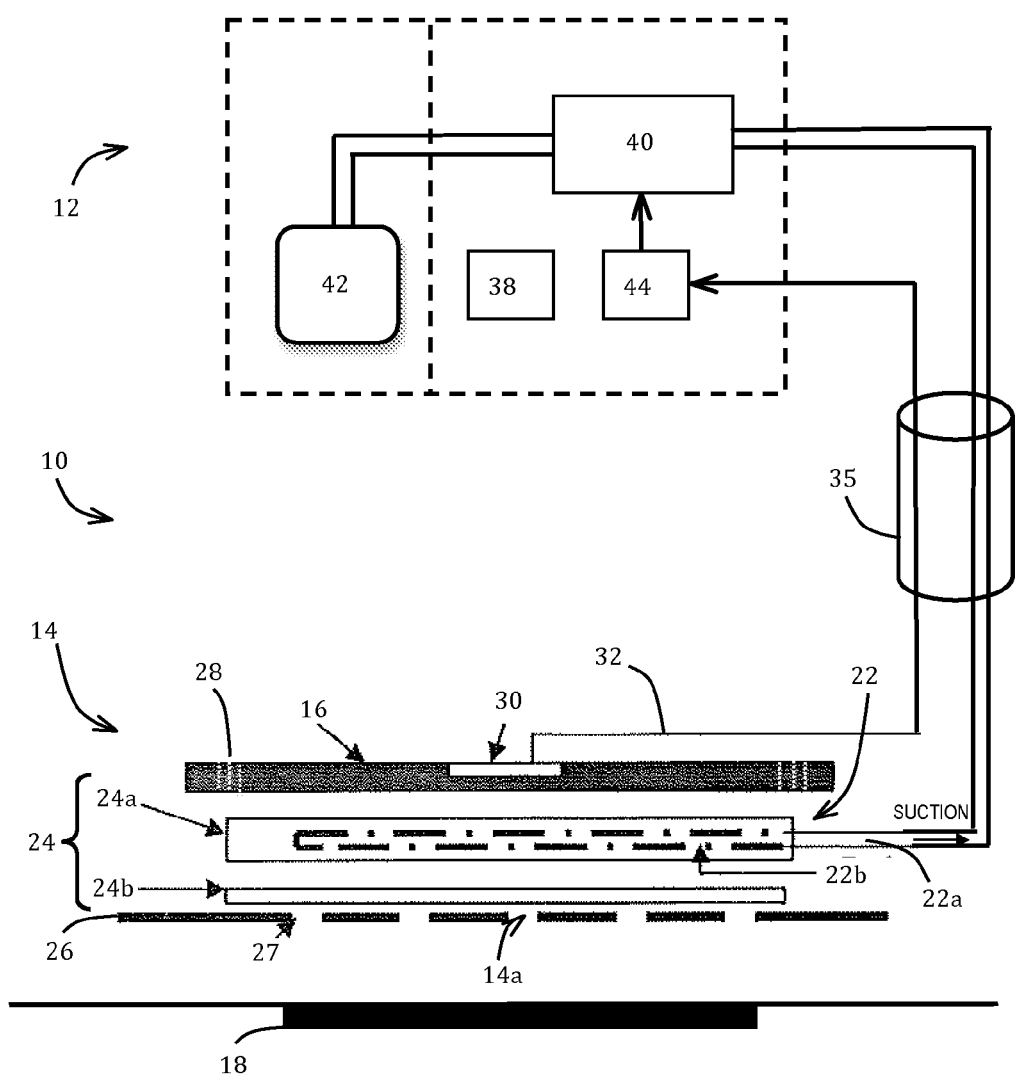
FIG. 1 is a schematic block diagram of a first embodiment of wound management system, including a wound dressing and an aspiration unit for aspirating excess exudate from the wound dressing, the diagram including a schematic sectional view of wound dressing components.

Preferred embodiments of the invention are now described with reference to the drawings. The same reference numerals are used to depict the same or equivalent features in each embodiment.

First Embodiment

Referring to FIG. 1, a wound management system 10 generally comprises a wound dressing 14 and an aspiration unit 12 for applying suction to the wound dressing 14 to aspirate excess exudate. The field of wound dressings with exudate aspiration is quite unique, and very different from the field of, for example, urine removal. Urine is usually discharged as a surge of liquid, and a urine removal system should remove all urine to leave the skin dry in order to avoid irritation and infection. In contrast, wound exudate is not discharged in a surge, and it is not desirable to remove all of the wound exudate. The exudate contains a complex mixture of bioactive molecules that have both positive and negative effects. While removal of excess exudate is desirable, removal of all exudate may hinder rather than aid wound healing. Instead, the present embodiment aims to manage the amount of wound exudate, and remove excess from the wound site. Also, the present embodiment aims to avoid maintenance of negative pressure at the wound site, in order to avoid the potential complications associated with topical negative pressure.

The wound dressing 14 is preferably attachable to the patient's skin by means of an adhesive pad 26. The absence of substantial negative pressure at the wound site 18 means that the wound dressing 14 will not be held in position by substantial suction, and the adhesive pad 26 compensates to positively locate the wound dressing 14. In the form illustrated in FIG. 1, the adhesive pad 26 extends over the wound site 18, and has perforations or apertures 27 to permit passage of exudate from the wound site 18 into the wound dressing 14. In the form illustrated in FIG. 2, the adhesive pad 26 has a closed loop shape that circumscribes the periphery of the wound site 18. The adhesive pad 26 is made of a skin-friendly medical grade adhesive. Examples of suitable adhesives include pressure-sensitive adhesives that may be any of hydrocolloid, polyurethane, acrylic, thermoplastic elastomer (TPE), hydrogel, or silicone-based. The portion of the wound dressing 14 communicating with the wound site 18 is referred to herein as the wound interface region 14a.

The wound dressing 14 generally comprises a cover 16, a liquid handling material 24 (24a, 24b), and an aspiration port 22. The adhesive pad 26 may also form an integral part of the wound dressing 14, or it may be a separate component. The cover 16 extends over the wound site 18, and overlaps healthy periwound tissue. The cover 16 is impermeable to liquids and/or water vapor, in order to contain exudate, and to prevent ingress of external liquids. The cover may, for example, be made of flexible polyurethane (PU) foam, polyurethane (PU) foam laminated with a film, or low durometer polyethylene (PE) foam.

The liquid handling material 24 may serve as any one, or any combination of two or more, of (i) a pressure barrier, (ii) a material for collecting liquid exudate by sorption, and allowing the exudate to be pumped away under suction, (iii) a material for maintaining a moist environment at the wound surface while permitting excess exudate to be pumped away under suction.

The liquid handling material 24 (24a, 24b) may, for example, be a material for sorbing (adsorbing or absorbing) exudate without gelling. Such a material may be non-woven and/or foam. Such a non-woven could be hydrophobic or hydrophilic, synthetic or natural. The liquid handling material 24 (24a, 24b) may allow liquid to wick in all directions, in order to permit transfer of liquid within the liquid handling material 24 (24a, 24b) to the point of aspiration. The liquid handling material 24 (24a, 24b) may alternatively be, or comprise, a material that forms a cohesive gel when wetted with wound exudate. Such gelling material may be a fibrous blend or fibrous material (e.g., a non-woven). An example is the wound contact layer of the Versiva® dressing (ConvaTec Inc., Skillman, N.J.) or a fibrous mat of sodium carboxymethylcellulose. A fibrous mat of sodium carboxymethylcellulose is available as AQUACEL® dressing from ConvaTec Inc., as is a similar dressing further including silver. Other exemplary materials for the liquid handling material 24 include Medicel™ and Carboxflex™ (which provides an odor absorbent layer with fibrous material for wicking liquid away from the odor absorbent).

In a further form, a combination of both a non-gelling liquid handling material 24a and a (fibrous) gelling material 24b may be used, for example, in distinct layers. The materials 24a, 24b may be bonded to each other, or they may be contained as separate layer components within the wound dressing 14. The layer closest to the wound site 18, for example, the gelling material 24b, may be perforated to allow excess exudate to be absorbed by another layer, for example, the non-gelling material 24a. In such a combined arrangement, the gelling material 24b mainly provides the property (iii) mentioned above, while the non-gelling material 24a mainly provides the properties (i) and/or (ii).

The aspiration port 22 comprises suitable tubing 22a (e.g., silicone tubing) extending into the wound dressing 14 for delivering aspiration suction from the aspiration unit 12. In the form illustrated, the tubing 22a extends through a peripheral side edge of the wound dressing 14, although the tubing 22 could enter the wound dressing 14 at any suitable point, such as passing through an aperture in the cover 16. The tubing 22a comprises an aspiration interface portion 22b, comprising one or more apertures or perforations, through which the suction is applied to the wound dressing 14 for drawing away the excess exudate, described later.

A preferred feature of the present embodiment is that the wound dressing 14 is configured such that the wound interface region 14a is not substantially exposed to the negative pressure applied to the aspiration port 22, and so the wound site 18 is also not substantially exposed to such negative pressure. As used herein, the negative pressure is defined as a pressure differential with respect to ambient atmospheric pressure. The magnitude of the negative pressure refers to the magnitude of difference with respect to the ambient atmospheric pressure. A large negative pressure means a large pressure difference from atmospheric pressure, and a smaller negative pressure means a pressure closer to atmospheric pressure. Conventional TNP devices maintain a negative pressure between 75 mm Hg to 125 mm Hg continuously or intermittently. Atmosphere pressure is equal to 760 mm Hg (i.e., 101K Pascal or 1,013 mbar). The wound dressing 14 is configured such that, in use, any negative pressure at the wound interface region 14a is not more than (and preferably less than) about 10% of the negative pressure (75 mm Hg) applied at the aspiration port 22, preferably not more than about 5% (38 mm Hg) more preferably not more than about 4% (30 mm Hg), more preferably not more than about 3% (23 mm Hg), more preferably not more than about 2% (15 mm Hg), and more preferably not more than about 1% (7.6 mm Hg).

Avoiding exposure of the wound site 18 (wound interface region 14a) to substantial negative pressure can avoid many of the problems of the prior art. In particular, it can avoid the issues associated with new tissue growth drawn into the wound dressing components, and the pain and potential tissue damage upon removal or replacement of the wound dressing 14. It can also avoid drying out of the wound exudate.

The present embodiment avoids negative pressure at the wound interface region 14a, by one or both of:
(i) the provision of a pressure barrier within the wound dressing 14, and/or
(ii) the provision of one or more atmospheric vents or porous materials for equalizing the pressure at the wound interface region 14a.

As mentioned above, the pressure barrier may be implemented by at least a portion of the liquid handling material 24.

The aspiration interface portion 22b of the port tubing 22a is separated from the wound interface region 14a by at least a portion of the liquid handling material 24, for example, the non-gelling material 24a. The pressure barrier characteristic is provided, for example, by virtue of suitably small pores in the liquid handling material. In the form illustrated in FIG. 1, the aspiration interface portion 22b is disposed within the exudate handling layer 24, for example, the non-gelling layer 24a. In the form illustrated in FIG. 2, the aspiration interface portion 22b is disposed behind the exudate handling material 24, and is sealed by an impermeable membrane 22c such that the aspiration interface portion 22b communicates with the interior of the wound dressing 14 only via the liquid handling material 24.

Additionally or alternatively, atmospheric vents 28 are provided for equalizing the pressure at the wound interface region 14a. The atmospheric vents 28 may be capillaries or pores in the cover 16. Atmospheric vents 28 can be also made from porous materials, such as air-breathable membranes, air-breathable nonwovens, air-breathable foams, etc. Among these porous materials, air-breathable membranes and air-breathable non-wovens are preferred due to their ability of preventing the liquid and water vapor from flowing through (e.g., using hydrophobic treatment) while allowing the air to pass. Air-breathable membrane can, for example, be made from polymers selected from high density polyethylene (HDPE), ultra high molecular weight polyethylene (UHMWPE), polypropylene (PP), poly(vinylidene fluoride) (PVdF), poly(tetrafluoro ethylene) (PTFE). These polymers can be sintered or stretched to create the porous structure to allow the air to flow through. These porous materials, such as membranes and non-wovens, can optionally be hydrophobic treated to impart or increase the resistance to liquids (i.e., exudate) and moisture vapor, but the material remains permeable to air. These porous materials can be also made into various forms, such as a low profile rigid part, a semi-rigid part, or a flexible membrane. The air flow rate of atmospheric vent and porous material is at least 5 cc/min at 10 mbar, preferably at least 50 cc/min at 10 mbar, and more preferably at least 100 cc/min at 10 mbar. The cover is impermeable to water vapor or liquids in order to prevent liquid ingress into the wound dressing 14, and to stop the passage of exudates. The atmospheric vents 28 communicate with the interior of the wound dressing 14, in particular with the wound interface region 14a.

In use, wound exudate is sorbed (adsorbed and/or absorbed) by the liquid handling material 24. Upon application of suction via the port 22, a localized pressure gradient in at least a portion of the liquid handling material 24 draws or wicks excess exudate to the aspiration interface portion 22b at which the exudate is aspirated away via the port 22. The pressure at the wound interface region 14a remains at substantially atmospheric pressure by virtue of the pressure barrier characteristic of the liquid handling material 24, or the atmospheric vents or porous materials 28, or a combination of above. In the absence of substantial negative pressure at the wound interface region 14a, the liquid handling material 24 plays a significant role in collecting exudate from the wound surface, and transporting the exudate to the aspiration interface portion 22b.

A liquid sensor 30 is provided for sensing exudate within the wound dressing 14, and for generating a sensor signal 32 for controlling the aspiration unit 12. The liquid sensor 30 may be responsive to the proximity and/or the quantity of liquid. The liquid sensor 30 may be separate or separable from the wound dressing 14, enabling replacement of the wound dressing 14 without having to use a new sensor 30. In such a case, a means is preferably provided for releasably attaching the sensor 30 to the wound dressing 14. Alternatively, the liquid sensor 30 may be permanently attached to the wound dressing 14 to form an integral unit. With permanent attachment, the liquid sensor 30 is intended to be disposed of with the wound dressing 14.

Additionally or alternatively, sensor 30 can be a pressure sensing unit responsive to the set point pre-determined in order to avoid exposure of the wound site 18 (wound interface region 14*a*) to substantial negative pressure.

The sensor signal 32 is typically an electrical or electronic signal. However, other signal forms may be used as desired, for example, optical.

The sensor 30 may generate output signal 32 that varies in accordance with the sensed parameter(s). For example, the output signal 32 may be a varying analog signal (e.g., variable current or voltage), or the output signal 32 may be a digital signal (e.g., a quantized representation, or a variable pulsed representation). Alternatively, the sensor signal 32 may be a logical (e.g., binary, or on/off) signal indicating whether or not the sensed parameter exceeds or is below one or more thresholds.

The liquid sensor 30 is preferably a non-contact sensor that is able to detect the presence or proximity of liquid without contact with the liquid. The feature of the liquid sensor 30 being a non-contact sensor provides significant advantages because: (i) the non-contact approach automatically avoids any concerns about passing an electrical current through liquid in contact with the skin 20 and wound site 18. Instead, there is no direct contact between the liquid sensor 30 and the liquid; (ii) the non-contact approach means that the liquid sensor 30 is not contaminated by touching the liquid exudate. This allows the liquid sensor 30 easily to be reused with a different wound dressing 14; and (iii) the non-contact approach means that the liquid sensor 30 does not itself have to be in a sterile condition before use, thus avoiding the difficulty of, or risk of damage when, sterilizing the wound management system 10 that does interface intimately with the body. The feature of the liquid sensor 30 being coupled to the aspiration unit 12 by an electrical connector avoids the expense and fragility associated with using an optical fiber connection.

An optional feature of the invention is that the liquid sensor 30 is separate from, or at least separable from, the wound dressing 14. The wound dressing 14 may be a disposable item that may be manufactured inexpensively, and disposed of after a single use, or a limited number of uses. The liquid sensor 30 may be more expensive, but may be intended to be used multiple times, preferably, with a sequence of different wound dressings 14 used during wound treatment. This enables the wound management system 10 to be produced and used very cost efficiently, since the disposable components are generally low cost. The higher cost components may be used multiple times, and may require infrequent replacement. In one form, the liquid sensor 30 is a universal device that may be used with any of a plurality of different types of wound 14

Alternatively, the non-contact sensor 30 may be permanently attached to the wound dressing 14, and not be a reusable item.

The liquid sensor 30 can take a variety of different forms. The liquid sensor 30 is optionally selected from: a capacitance sensor; an ultrasonic sensor; and a piezo-electric (or piezo-resonant) sensor. A capacitance sensor detects proximity of liquid according to changes in the dielectric effect of liquid proximity, compared to air proximity. The dielectric effect affects the electric field in the active zone around the sensor, and thus, the effective capacitance in the sensor. The capacitance is monitored by any suitable capacitance sensing circuit (not shown), such as an RC oscillator whose oscillation frequency and/or whether oscillation occurs, is dependent on the value of a resistor in combination with the effective capacitance of the sensor. The oscillation in turn triggers an output stage, coupled to an output amplifier, to generate an output signal indicative of liquid presence. The capacitance sensing circuit is preferably disposed near or at the liquid sensor 30 (e.g., as part of the liquid sensor 30 itself), or the capacitance sensing circuit can be disposed at the aspiration unit 12, or at a point along electrical connector. A suitable capacitance sensor and capacitance sensing circuit are described in U.S. Pat. No. 5,576,619, the contents of which are hereby incorporated by reference.

The ability to detect liquid has been tested using a capacitance "smart" sensor from SIE Sensors. The sensor 30 of dimension 35 mm (length)×22 mm (width)×10 mm (height) was affixed to the external wall of a wound dressing 14. The sensor 30 detected the presence of two test liquids, water and saline solution, as soon as the liquid was introduced, and provided an activation signal to the aspiration unit 12 within milliseconds. The electric field from the sensor 30 is able to penetrate a wide variety of plastic components (e.g., polyethylene (PE), polypropylene (PP) and acrylics), either transparent or opaque, with great sensitivity.

An ultrasonic sensor works using the principle of sonar at the ultrasonic frequency range. A transducer is resonated at a set frequency to convert electric energy into ultrasonic frequency range acoustic energy. The ultrasonic acoustic waves are emitted towards a liquid collection region. Energy is reflected either from the walls if the region is empty of liquid, or from liquid if present in the region. By measuring the time delay for reflected waves to arrive, and comparing this to one or more pre-calibrated time delays taken when the liquid collection region is empty, the presence of liquid can be reliably and quickly detected. An example of ultrasonic liquid sensor is described in U.S. Pat. No. 3,960,007, the content of which is incorporated herein by reference. A commercially available ultrasonic sensor is made available by ZEVEX Inc.

A piezo-electric or piezo-resonant sensor also uses high frequency, e.g., ultrasonic energy or acoustic signal, in a similar way to the ultrasonic sensor described above. The ultrasonic or acoustic signal could penetrate either transparent or opaque plastic walls. An example of piezo-electric sensor is described in U.S. Pat. No. 3,948,098, the content of which is incorporated herein by reference.

The ability to detect liquid has been tested with a piezo-resonant sensor obtained from GEMS Sensors. The sensor 30 of diameter 40 mm was attached to the external wall of the wound dressing 14, and detected the presence of liquid as soon as introduced.

Figure 2:
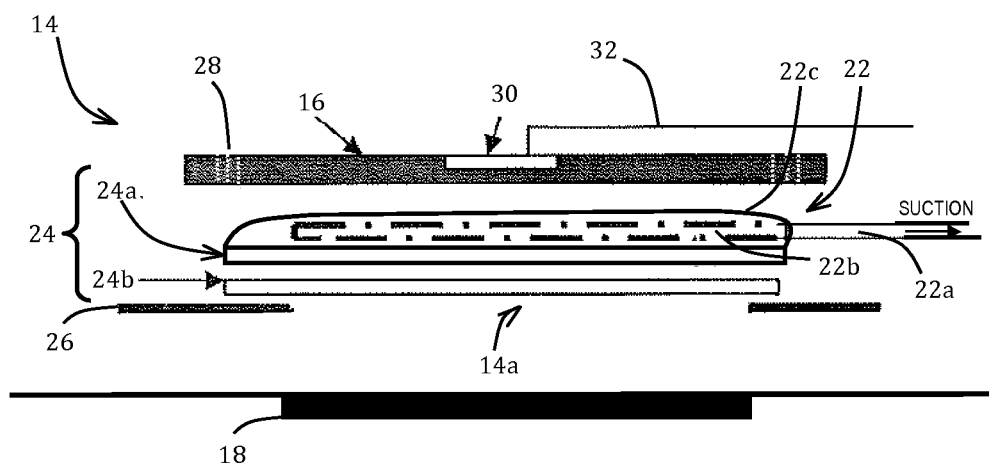
FIG. 2 is a schematic sectional view showing a modified version of the wound dressing of FIG. 1.

With the arrangement illustrated in FIGS. 1 and 2, the liquid sensor 30 is disposed outside the wound dressing 14, or at least outside a liquid collection region of the wound dressing 14. The cover 16 is typically made of material through which the sensing electric field can pass in the case of a capacitance sensor, or through which an ultrasonic vibration can pass in the case of an ultrasonic and/or piezo-electric sensor. The cover 16 may be made suitably thin to provide the sensor 30 with the desired sensitivity to liquid within the wound dressing 14. Alternatively, the cover 16 may include a window portion made of material through which the electric field or ultrasonic vibration can pass easily if the entire cover 16 is not made of such a material. In an alternative embodiment, the housing of the wound dressing 14 can be shaped into a pocket with or without membrane, for receiving and retaining a capacitive, ultrasonic or piezo-electric non-contact liquid sensor 30. Such a design also increases the interface area between the sensor 30 and the liquid collection region of the wound dressing 14.

In an alternative embodiment, the sensor 30 is an electro-optical sensor. The cover 16 comprises a window region (not shown) made of material that is transparent to the optical radiation used by the electro-optical sensor. For example, the optical radiation may be in the infra-red range, and/or the visible range, and/or ultra-violet range. The term "optical" as used herein means that the radiation lies in a frequency range that obeys substantially the laws of optics. The electro-optical sensor comprises an electro-optical emitter, an electro-optical receiver, and sensing circuitry for detecting the presence of liquid according to the electrical output of the electro-optical receiver. The sensing circuitry is preferably disposed at the liquid sensor 30 (e.g., as part of the liquid sensor 30), or the sensing circuitry is disposed at the aspiration unit 12, or at a point along electrical connector 35. An example electro-optical liquid sensor is described in U.S. Pat. No. 4,354,180, the content of which is incorporated herein by reference.

If preferred, the liquid sensor 30 may be disposed at a position (not shown) in contact with exudate inside the wound dressing 14, even if the sensor 30 does not rely on direct contact to detect the liquid. Such a possibility also enables the use of a contact-based sensor 30 instead of a non-contact sensor 30. An example of a contact-based sensor 30 is an electrical resistance sensor that detects liquid by conductance between electrodes in contact with the liquid.

In the case that the liquid sensor 30 is separate from, or at least separable from, the wound dressing 14, the liquid sensor 30 may be held in an operative position with respect to the wound dressing 14 by a detachable attachment device (not shown) for releasably attaching the liquid sensor 30 to the wound dressing 14. For example, the detachable attachment device could comprise a peelable adhesive, or a peelable mechanical fastener, such as Velcro®, or a mechanical coupling based on interference fitting, or other mechanical means.

A flexible electrical connector or conduit 35 couples the wound dressing 14 to the aspiration unit 12. A releasable connector or an easy release coupling may be provided at one end, or both ends, of the flexible electrical connector 35. The flexible electrical connector 35 may be regarded as part of the aspiration unit 12 and/or part of the wound dressing 14. The flexible conduit 35 links the port 22 to a suction source 40 within the aspiration unit 12. The aspiration unit 12 comprises a power supply 38, an electronic control unit 44, and the suction source 40. The power supply 38 is selected as one or more of: a replaceable battery, a rechargeable battery, radiation collection panels, and a main power supply. Preferably, the power supply 38 includes a combination of a rechargeable battery and a main power supply; such a combination allows portable operation when the wound management system 10 is not connected to a main power supply, as well as automatic recharging of the battery when the wound management system 10 is coupled to a main power supply. Additionally or alternatively, the power supply 38 includes radiation collection panels, such as photovoltaic panels or cells for generating electricity from ambient light, which can improve autonomy of operation or for charging the rechargeable battery. The power supply 38 may provide power for any one or more of: the electronic control unit 44, the liquid sensor (if needed) 30 and any power needed by the suction source 40. In the present embodiment, the suction source 40 is an electric pump that operates under control of the electronic control unit 44. The pump 40 could be a suction device based on diaphragm, peristaltic, volume displacement, spring, gravity, siphon, heat-recoverable metal drive, or an in-line pump. The flexible conduit 35 is coupled through the pump 40 to a liquid collection chamber 42 for collecting exudate removed from the wound dressing 14. The liquid collection chamber 42 may either be separate from the aspiration unit 12 (as illustrated) and coupled thereto with a suitable connector, or the liquid collection chamber 42 may be integral with and/or housed in the aspiration unit 12 (arrangement not shown). In an alternative form, instead of a pump 40 directly applying suction to the flexible conduit 35, the suction source 40 may comprise a vacuum chamber charged with a low pressure vacuum, and an electronically controlled valve for controlling application of suction from the vacuum chamber to the flexible conduit 35. A pump may be provided for charging the vacuum chamber with the vacuum.

In the present embodiment, it is preferred that application of aspiration suction is controlled responsive to the sensor signal 32. This further avoids subjecting the wound dressing 14 to negative pressure unless the sensor 30 detects the presence of sufficient liquid exudate within the wound dressing 14. Thus, not only is the wound dressing 14 configured not to subject the wound site 18 to substantial negative pressure from the aspiration port 22, but optionally also the application of negative pressure at the aspiration port itself 22 is also reduced, suction being applied only when judged necessary in response to the sensor signal 32 from the liquid sensor 30.

It will be appreciated that although the wound dressings 14 shown in FIGS. 1 and 2 differ in two respects (i.e., the position of the aspiration interface portion 22b, and the configuration of the adhesive pad 26), these configurations may be intermixed as desired.

Second Embodiment

Figure 3:
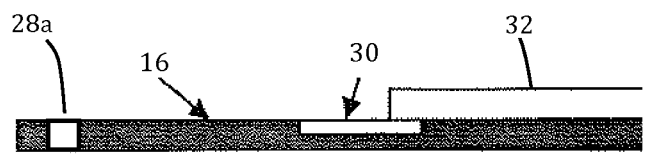
FIG. 3 is a schematic diagram illustrating a vacuum relief means in the cover for the second embodiment of the wound dressing.
Figure 4:
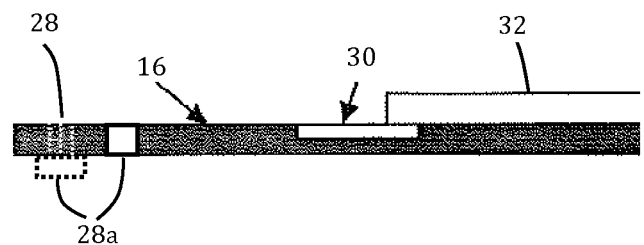
FIG. 4 is a schematic diagram showing a modified arrangement of the vacuum relief means.

The second embodiment has the same construction as described above, but further refines properties of the atmospheric vent 28. FIGS. 3 and 4 illustrate only the material carrying the vent 28, such as the backing or cover 16, the other elements of the wound dressing 14 being as in any of the other embodiments. Additionally or alternatively to the vent previously described, the atmospheric vent 28 comprises one or more vacuum relief means 28a (i.e., pressure relief means) which allows air to flow into the wound dressing 14 for equalizing and/or stabilizing the interior space of the wound dressing 14 when the amount of negative pressure inside the wound dressing 14 is higher than the set point. Vacuum relief means 28a may, for example, comprise check valve, duckbill valve, umbrella valve, solenoid valve, minivalveball, or a combination of any of these. In FIG. 3, the vacuum relief means 28a replaces the previous porous vent arrangement 28. In FIG. 4, the vacuum relief means 28a is used in addition to the porous vent arrangement 28 previously described, in order to provide additional pressure relief via a parallel vent path should the internal negative pressure exceed the preselected limit. Additionally or alternatively, as depicted by the broken line, the vacuum relief means 28a may be used with the atmospheric vent 28, and mounted on the interior side of the cover 16 and/or vent 28, or on the exterior side if preferred.

Conventional TNP devices maintain a negative pressure between 75 mm Hg to 125 mm Hg continuously or intermittently. Atmosphere pressure is equal to 760 mm Hg (i.e., 101K Pascal or 1,013 mbar). The wound dressing 14 is configured such that, in use, any negative pressure at the wound interface region 14a is not more than about 10% of the negative pressure (75 mm Hg or 100 mbar) applied at the aspiration port 22, preferably not more than about 5% (38 mm Hg or 50 mbar) more preferably not more than about 4% (30 mm Hg or 40 mbar), more preferably not more than about 3% (23 mm Hg or 30 mbar), more preferably not more than about 2% (15 mm Hg or 20 mbar), and more preferably not more than about 1% (7.6 mm Hg or 10 mbar).

Third Embodiment

Figure 5:
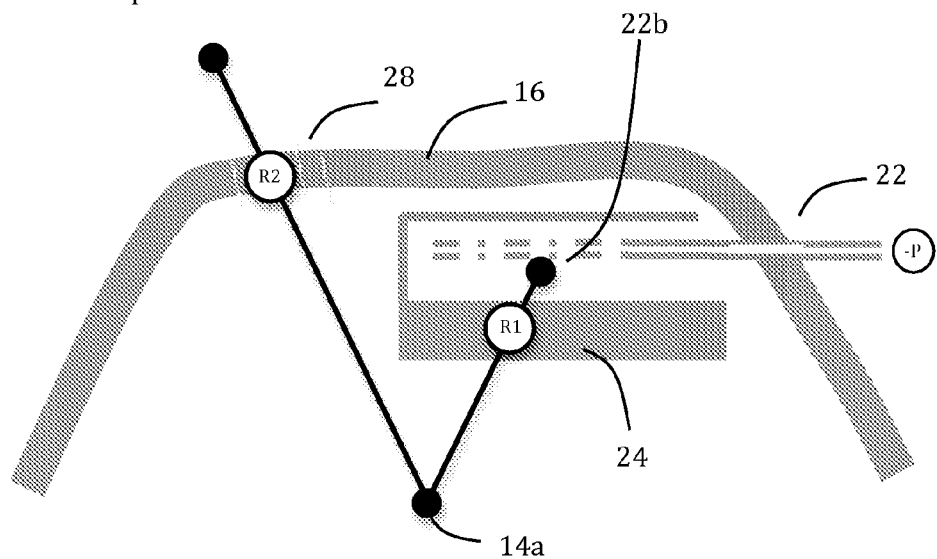
FIG. 5 is a schematic diagram illustrating flow resistances and pressure drops within a third embodiment of the wound dressing.
Figure 5:
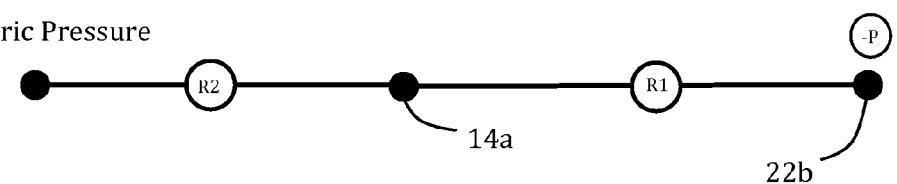

The third embodiment has the same construction as described for any of the preceding embodiments, but further refines properties of the pressure barrier, and the atmospheric vent 28. Air flow resistance is defined as the pressure drop across a specimen divided by the flow rate. A material with a higher air flow resistance requires a higher pressure gradient in order to achieve the same air flow rate. Referring to FIG. 5, the pressure barrier is provided by the non-gelling material 24a of the liquid handling material 24, which has a first resistance R1 to gas flow therethrough, by virtue of small pores in the material to which the gas flow is confined. The first resistance R1 is measured between the aspiration interface portion 22b and the wound interface region 14a. The atmospheric vents 28 are provided by breathable pores or porous materials in the cover 16, which has a second resistance R2 to gas flow therethrough by virtue of their size of opening, porous structure or design. The second resistance R2 is measured from one face of the cover 16 to the other face. A feature of the third embodiment is that first resistance R1 is substantially greater than the second resistance R2. Preferably, the first resistance R1 is at least 10 times greater than the second resistance R2, more preferably, at least 100 times greater, more preferably at least 500 times greater.

As shown in FIG. 5, the first and second flow resistances R1 and R2 may define a serial flow path from the aspiration interface portion 22b, through the first flow resistance R1 (of the liquid handling material 24a) to the wound interface region 14a, and through the second flow resistance R2 (of the cover 16) to the ambient atmosphere outside the wound dressing 14. The negative pressure (−P) is applied at the aspiration interface portion 22b. The pressure at the wound interface region 14a is influenced by two neighboring pressures, namely the negative pressure −P separated by the flow resistance R1 of the liquid handling material 24a, and the ambient external atmosphere separated by the flow resistance R2 of the atmospheric vents or porous materials 28. Assuming there is no flow from the wound site 18, respective negative pressure drops occur across each of the flow resistances R1 and R2 in relative proportion to the ratio of these flow resistances, $(R1)/(R1+R2)$, and $(R2)/(R1+R2)$, respectively. The pressure to which the wound interface region 14a is subjected is $(-P)*(R2)/(R1+R2)$. However, since the second resistance R2 (of the cover 16) is much smaller than the first resistance R1 (of the liquid handling material 24a), this ensures that the pressure at the wound interface region 14a is very close to atmospheric. The majority of the negative pressure is dropped across the first flow resistance R1 of the liquid handling material 24a, confirming the effect as a pressure barrier. There is virtually no pressure difference dropped across the second flow resistance R2 (of the cover 16), confirming that the cover 16 acts as an atmospheric vent 28, and that the pressure at the wound interface region 14a is close to atmospheric.

It will be appreciated that, when the liquid handling material 24a contains liquid exudate, the first resistance R1 to flow is further increased by virtue of less open area available for air flow, and the suction loss resulting from the work to move the exudate towards the aspiration interface portion 22b.

Typical values of the air flow rate of atmospheric vent 28 or porous material are at least 5 cc/min at 10 mbar, preferably at least 50 cc/min at 10 mbar, and more preferably at least 100 cc/min at 10 mbar. Therefore, the second air flow resistance R2 is less than 2 mbar*min/cc, preferably less than 1 mbar*min/cc, and more preferably less than 0.1 mbar*min/cc. The first air flow resistance R1 is at least 10 times greater than the second resistance R2, more preferably, at least 100 times greater, and more preferably at least 500 times greater. Therefore, the first air flow resistance R1 across the pressure barrier is less than 20 mbar*min/cc, preferably less than 200 mbar*min/cc, and more preferably less than 1,000 mbar*min/cc.

Fourth Embodiment

The fourth embodiment has the same construction as the first, second and/or third embodiments, but further incorporates properties of a liquid-trap-pressure-barrier. Such a barrier incorporates small pores that, when wetted by liquid exudate, are closed by the surface tension of the liquid to act as a barrier to air flow. The pore size may be of the order of about 5 to about 30 microns, more preferably from about 15 to about 20 microns. Once the barrier has been wetted, it may support a negative pressure differential of typically 5 inches to 60 inches of water without permitting air to pass. Depending on the size of the pores, the suction pressure that can be applied without air passing through the barrier varies. Such a liquid-trap-pressure-barrier is liquid permeable, but is impermeable to air flow. Thus, if negative pressure is applied to one side of the pressure barrier and the barrier has been wetted, whenever liquid exudate comes into contact with the barrier it is drawn by the negative pressure through the barrier, without application of the significant negative pressure to the wound interface region 14a. The use of such a liquid-trap-pressure-barrier allows an effective removal of exudate across the wound dressing 14 without the application of significant negative pressure. Additionally or alternatively, an atmospheric vent 28, selected from microporous holes, capillary holes, a porous material, or a vacuum relief valve, can be used to maintain the pressure in the liquid handling material 24, thus effectively removing the exudate away from the wound dressing 14, without creating significant negative pressure.

The liquid-trap-pressure-barrier may be provided by a portion of the liquid handling layer material 24, such as the non-gelling material 24a. Alternatively, the liquid-trap-pressure-barrier may be implemented by an additional membrane at a suitable position between the aspiration interface portion 22b and the wound interface region 14a, for example sandwiched between the gelling material 24b and the non-gelling material 24a. The gelling material 24b can maintain a generally moist environment to prevent the membrane from drying out.

As long as the liquid-trap-pressure-barrier remains wet, and the negative pressure does not exceed a bubble threshold of the barrier (at which the effect of the liquid trap breaks down), a pressure barrier may be implemented that isolates the wound interface region 14a from the negative pressure applied at the aspiration port 22. The liquid-trap-pressure-barrier may be pre-wetted (either during manufacture or preparation by a caregiver), or it may become wet naturally during use of the wound dressing 14. The presence of the liquid sensor 30 may further enable the "wetness" within the wound dressing 14 to be monitored, and ensure that negative pressure is only applied from the aspiration unit 12 when a sufficient quantity of liquid has been detected within the wound dressing 14 to wet the barrier.

Further details of the characteristics of a liquid-trap-pressure-barrier may be found in U.S. Pat. No. 5,678,564, the content of which is hereby incorporated by reference.

Fifth Embodiment

In the first embodiment (and optionally the second, third, and fourth embodiments), the negative pressure applied by the aspiration unit 12 is generally predetermined, either by manufacture or by a user adjustable pressure regulator. The sensor signal 32 from the liquid sensor 30 is used to control the timing at which the application of negative pressure to the wound dressing 14 is turned on and/or off.

The fifth embodiment has generally the same construction as any of the preceding embodiments except that the electronic control unit 44 is additionally configured to regulate the magnitude of the negative pressure at the aspiration unit 12, responsive to the sensor signal 32. The magnitude of the negative pressure may be regulated by, for example, controlling the speed of a suction pump 40, or by controlling the aperture of a throttle valve. The throttle valve may of an analog type that opens to an adjustable amount, or it may be of a digital pulsed type where the effective aperture is controlled by the mark:space ratio and/or modulation of digital control pulses that alternate the valve between open and closed states.

Figure 6:
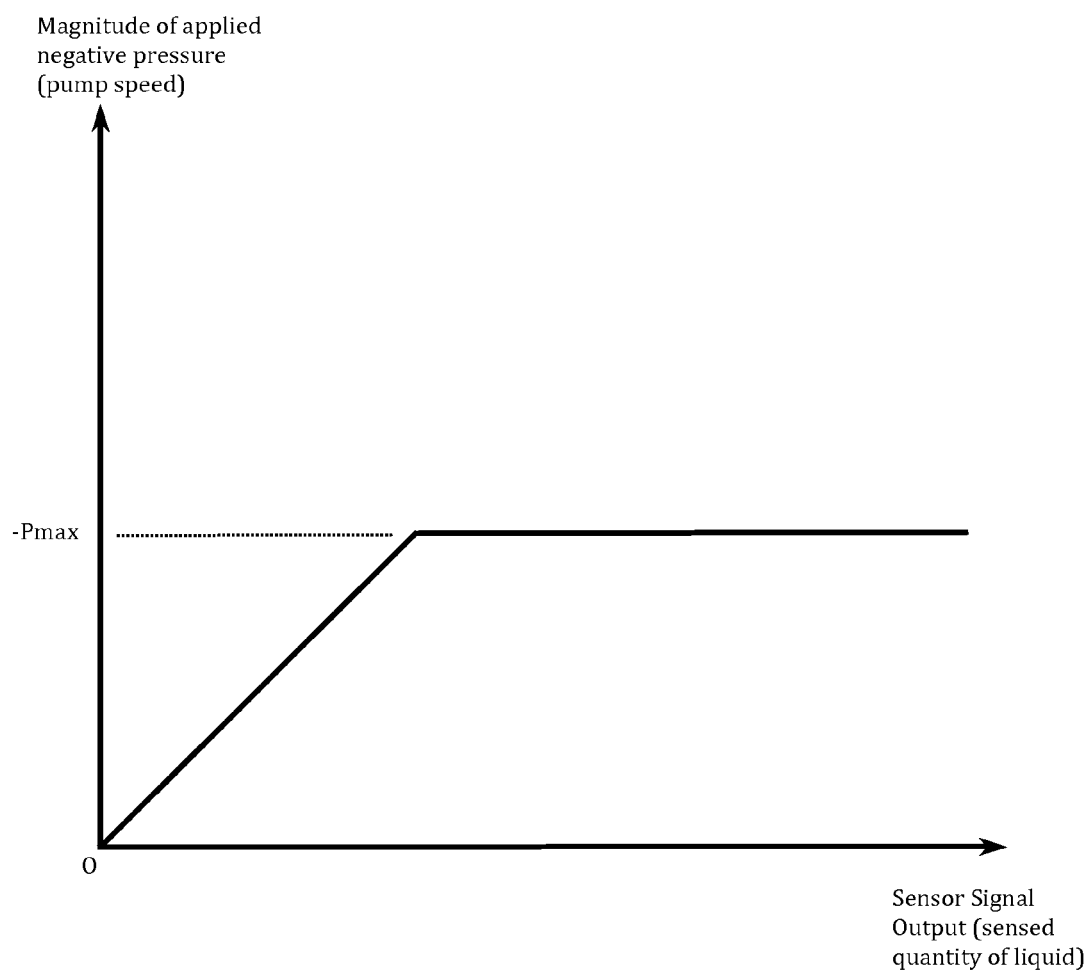
FIG. 6 is a schematic diagram showing for the fifth embodiment a relation between the signal from the liquid sensor, and responsive thereto the application of negative pressure.

Referring to FIG. 6, the magnitude of the negative pressure (−P) may be regulated from about zero (i.e., corresponding to atmospheric pressure) to a predetermined maximum (−Pmax), in accordance with the sensor signal 32. The correspondence may optionally be approximately linear, with the magnitude of the negative pressure plateauing at the predetermined maximum (−Pmax), although other correspondences or mappings may be used as desired.

The ability to regulate the magnitude of the negative pressure (−P) responsive to the sensor signal 32 from the liquid sensor 30 further avoids application of more negative pressure at the aspiration port 22 than is needed for removing the excess exudate. Depending on the design of the wound dressing 14, it may be easier to maintain a pressure barrier within the wound dressing 14 that is able to support a modest negative pressure at the aspiration port 22, and to isolate the wound interface region 14a from such modest negative pressure even for prolonged periods, than it is to support and isolate relative high negative pressure for short periods.

It will be appreciated that the wound dressing 14 and/or the wound management system 10 as described herein provides potential significant advantages compared to the prior art, and can address or mitigate many of the drawbacks of the prior art, especially in terms of efficient aspiration of wound exudate, without subjecting the wound site 18 to substantial negative pressure. Avoiding such negative pressure at the wound site 18 can avoid tissue growth into components of the wound dressing 14, and the associated discomfort and potential damage to tissue upon removal or replacement of the wound dressing 14. The invention can also provide efficient removal of excess exudate, while avoiding drying out of exudate at the wound site 18.

It will be appreciated that many modifications, improvements and equivalents may be within the scope of the invention as claimed.

I claim:

1. A wound dressing for an aspirated wound dressing system, the wound dressing comprising:
a wound interface region for contacting or facing a wound site;
an aspiration port for receiving suction for aspiration of wound exudate;
a liquid permeable pressure barrier disposed between the wound interface region and the aspiration port for substantially preventing application of negative pressure from the aspiration port to the wound interface region; and
a liquid sensor for sensing wound exudate liquid within the wound dressing and for controlling the application of suction through the aspiration port, wherein the air flow rate between the wound dressing to the surrounding atmosphere is at least 5 cc/min at 10 mbar pressure gradient.

2. A wound dressing for an aspirated wound dressing system, the wound dressing comprising:
a wound interface region for contacting or facing a wound site;
an aspiration port for receiving suction for aspiration of wound exudate;
a liquid permeable pressure barrier disposed between the wound interface region and the aspiration port for substantially preventing application of negative pressure from the aspiration port to the wound interface region; and
a liquid sensor for sensing wound exudate liquid within the wound dressing and for controlling the application of suction through the aspiration port; and
at least one atmospheric vent communicating with the wound interface region for equalizing the pressure at the wound interface region with ambient atmosphere, wherein the atmospheric vent is based on porous material selected from air-breathable membranes or air-breathable non-woven, and wherein the air flow rate of the atmospheric vent is at least 5 cc/min at 10 mbar pressure gradient.

3. A wound dressing for an aspirated wound dressing system, the wound dressing comprising:
a wound interface region for contacting or facing a wound site;
an aspiration port for receiving suction for aspiration of wound exudate;
a liquid permeable pressure barrier disposed between the wound interface region and the aspiration port for substantially preventing application of negative pressure from the aspiration port to the wound interface region; and
a liquid sensor for sensing wound exudate liquid within the wound dressing and for controlling the application of suction through the aspiration port; and
at least one atmospheric vent communicating with the wound interface region for equalizing the pressure at the wound interface region with ambient atmosphere, wherein the atmospheric vent is based on porous material selected from air-breathable membranes or air-breathable non-woven, and wherein the porous material is hydrophobic treated.

4. A wound dressing for an aspirated wound dressing system, the wound dressing comprising:
a wound interface region for contacting or facing a wound site;
an aspiration port for receiving suction for aspiration of wound exudate;
a liquid permeable pressure barrier disposed between the wound interface region and the aspiration port for substantially preventing application of negative pressure from the aspiration port to the wound interface region; and a liquid sensor for sensing wound exudate liquid within the wound dressing and for controlling the application of suction through the aspiration port; and at least one atmospheric vent communicating with the wound interface region for equalizing the pressure at the wound interface region with ambient atmosphere, wherein the pressure barrier has a first air flow resistance, and the atmospheric vent has a second air flow resistance substantially less than the first air flow resistance, whereby negative pressure is dropped substantially across the pressure barrier.

5. A wound dressing for an aspirated wound management system, the wound dressing comprising:

a wound interface region for contacting or facing a wound site;

an aspiration port for receiving suction for aspiration of wound exudate;

an atmospheric vent communicating with an interior of the wound dressing, the atmospheric vent comprising porous material that is permeable to air, and substantially impermeable to moisture vapor and liquid; and a liquid sensor for sensing wound exudate liquid within the wound dressing and controlling the application of suction through the aspiration port, wherein the air flow rate of the atmospheric vent is at least 5 cc/min at 10 mbar pressure gradient.

6. A wound dressing for an aspirated wound management system, the wound dressing comprising:

a wound interface region for contacting or facing a wound site;

an aspiration port for receiving suction for aspiration of wound exudate;

an atmospheric vent communicating with an interior of the wound dressing, the atmospheric vent comprising porous material that is permeable to air, and substantially impermeable to moisture vapor and liquid; and a liquid sensor for sensing wound exudate liquid within the wound dressing and controlling the application of suction through the aspiration port, wherein the porous material is hydrophobic treated.

* * * * *